United States Patent
Leigh et al.

(10) Patent No.: US 8,874,238 B2
(45) Date of Patent: Oct. 28, 2014

(54) CONFORMAL ELECTRODE PAD FOR A STIMULATING MEDICAL DEVICE

(75) Inventors: C. Roger Leigh, East Ryde (AU); Peter Gibson, South Coogee (AU)

(73) Assignee: Cochlear Limited, Macquarie University, NSW (AU)

(*) Notice: Subject to any disclaimer, the term of this patent is extended or adjusted under 35 U.S.C. 154(b) by 2011 days.

(21) Appl. No.: 11/562,734

(22) Filed: Nov. 22, 2006

(65) Prior Publication Data
US 2007/0150039 A1 Jun. 28, 2007

Related U.S. Application Data

(60) Provisional application No. 60/738,596, filed on Nov. 22, 2005.

(51) Int. Cl.
*A61N 1/05* (2006.01)
*A61N 1/36* (2006.01)

(52) U.S. Cl.
CPC ............. *A61N 1/0541* (2013.01); *A61N 1/0543* (2013.01); *A61N 1/36032* (2013.01)
USPC .......................................................... 607/137

(58) Field of Classification Search
CPC .................................................... A61N 1/0541
USPC ................................... 607/116, 118, 137, 152
See application file for complete search history.

(56) References Cited

U.S. PATENT DOCUMENTS 5,897,583 A * 4/1999 Meyer et al. ................... 607/116
2004/0010303 A1* 1/2004 Bolea et al. .................... 607/118

* cited by examiner

*Primary Examiner* — Christopher D Koharski
*Assistant Examiner* — Michael D Abreu
(74) *Attorney, Agent, or Firm* — K&L Gates LLP

(57) ABSTRACT

An ABI pad having a configuration and composition to provide the ABI pad with sufficient flexibility to permit the pad to be curved, molded or otherwise conformed to the cochlear nucleus, brainstem or other therapeutically-beneficial site, while ensuring the ABI pad maintains structural integrity over the anticipated operational life of the implant. The ABI pads are manufactured from silicone or other biocompatible material having a durometer sufficient to ensure the durability of the ABI pad over the anticipated operational life of the implant. To attain substantial flexibility, the thickness or cross section of the ABI pad is as minimal as possible to increase flexibility while not adversely affecting the noted durability of the pad. In one embodiment, the ABI pads are formed with an aperture in its interior region resulting in an ABI pad having minimal material mass while having sufficient structural integrity to reliably support the electrodes and associated wires. Thus, the ABI pads of the present invention may still be molded from, for example, industry standard 30 durometer silicone, and the wires and electrodes may be fabricated from industry standard platinum or a platinum/iridium alloy or other bio-compatible noble metals.

20 Claims, 13 Drawing Sheets

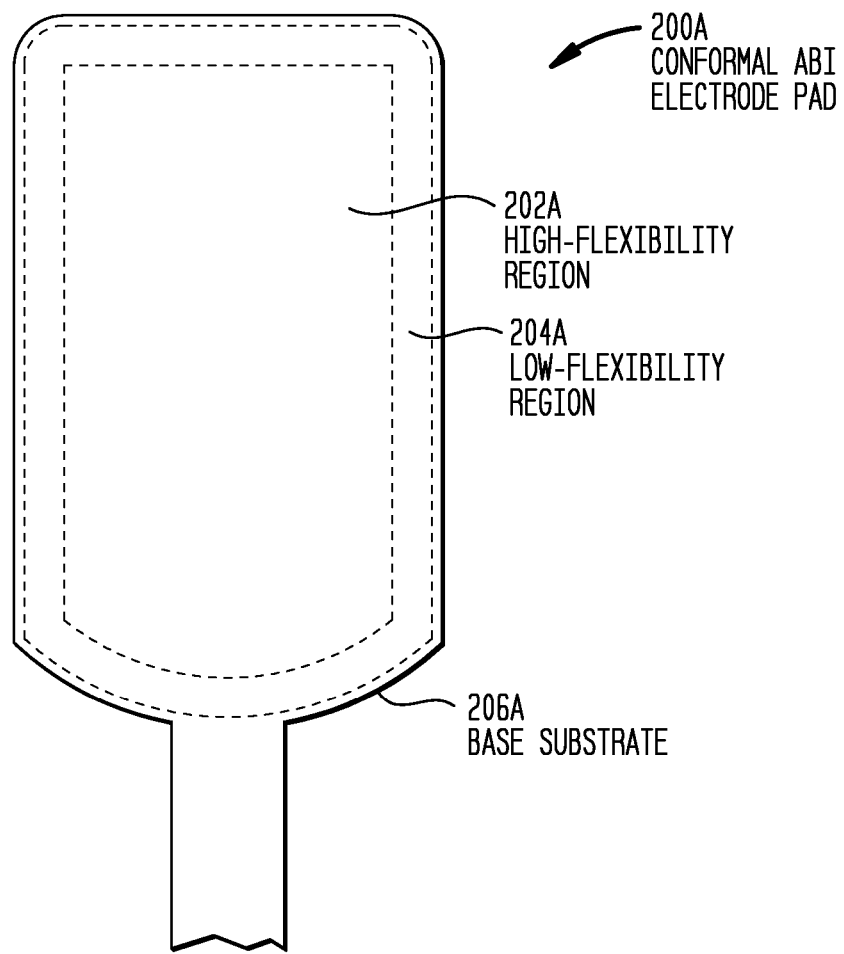

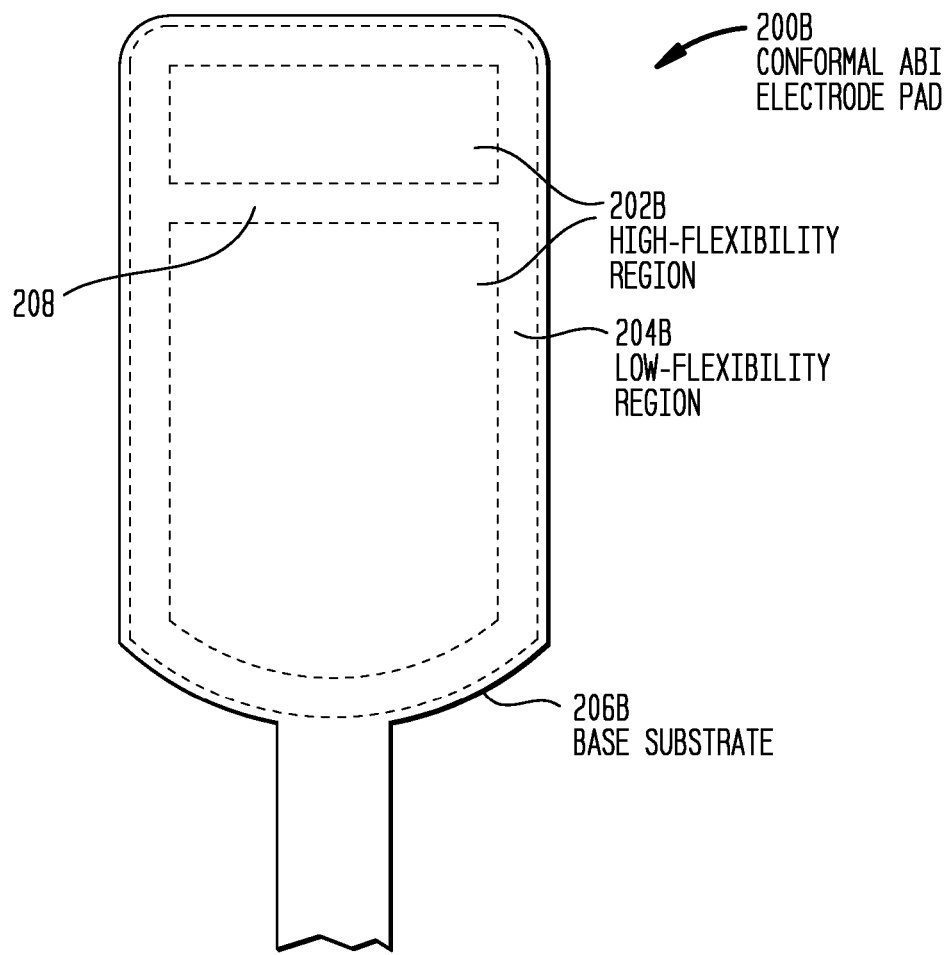

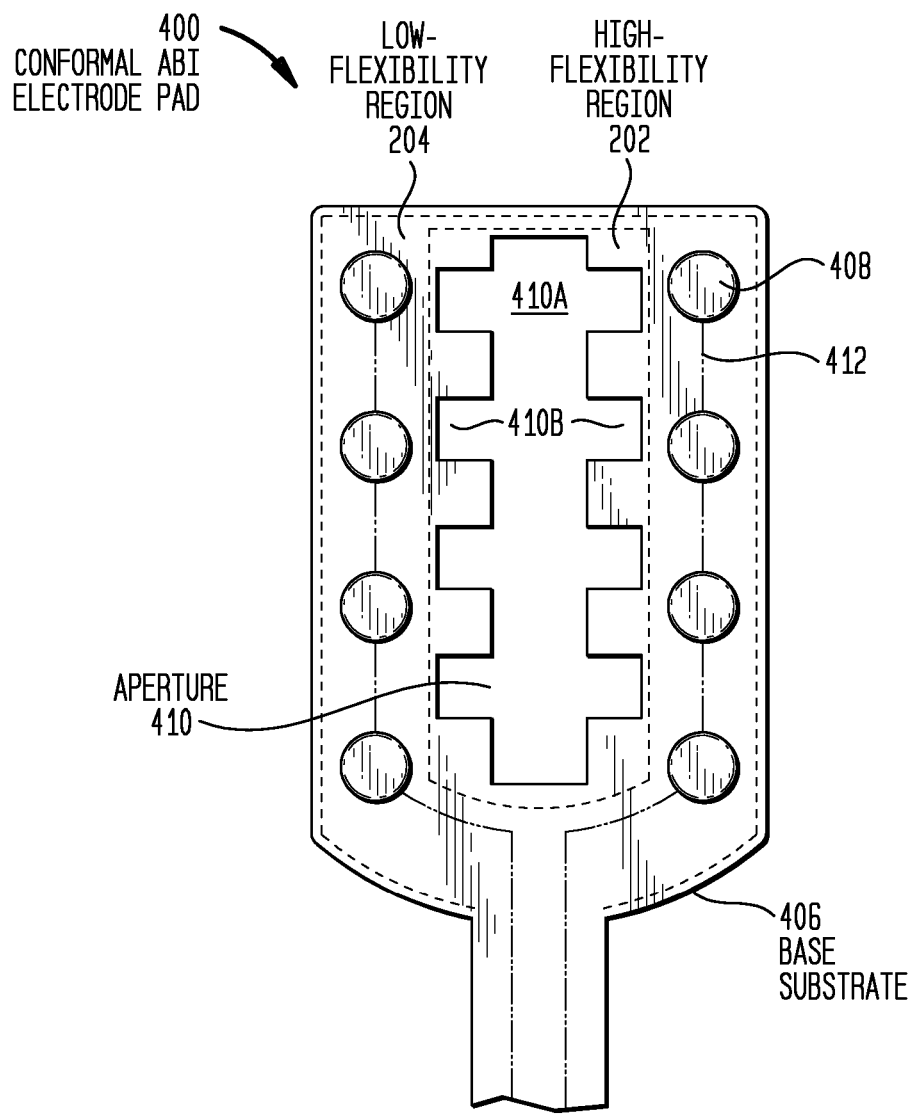

CONFORMAL ELECTRODE PAD FOR A STIMULATING MEDICAL DEVICE

CROSS-REFERENCE TO RELATED APPLICATIONS

This application makes reference to and claims priority from U.S. Provisional Patent Application No. 60/738,596 entitled "Flexible Auditory Brainstem Implant Pad," filed on Nov. 22, 2005, which is hereby incorporated by reference herein.

BACKGROUND

1. Field of the Invention

The present invention relates generally to electrodes for a stimulating medical device, and more particularly, to a conformal electrode pad for a stimulating medical device.

2. Related Art

There are several types of stimulating medical devices that use electrical signals to activate nerve or other tissue fibers in a patient to stimulate an activity or response. One type of such medical devices is the prosthetic hearing device. Prosthetic hearing devices are generally utilized to benefit individuals in which hearing has completely failed due to accident, illness or other effect or condition, or in which hearing is congenitally nonfunctional.

Prosthetic hearing devices apply one or more stimulation signals to the cochlea or auditory brainstem nucleus of a recipient to stimulate hearing. Such devices generally include a microphone that receives ambient sounds and a signal processor implementing a speech strategy which converts selected ambient sounds into corresponding stimulation signals. The signal processor controls an implanted unit to transmit the stimulation signals along an electrode array implanted within the recipient.

One such prosthetic hearing implant is a Cochlear™ implant (commonly referred to as Cochlear™ devices, Cochlear™ implant systems, and the like; hereinafter "cochlear implant"). Cochlear implants may be used when the inner ear (cochlea) is nonfunctional, but the neural auditory path which leads from the cochlea to the brain, is functional. Cochlear implants include an electrode array which is implanted in the cochlea to stimulate auditory nerves with electrical signals to produce a hearing sensation which can lead to speech comprehension.

Another type of implantable prosthetic hearing device is the auditory brainstem implant (ABI). The electrode array of an ABI is surgically implanted in the brain of a hearing impaired person who has damage to, or is lacking, the auditory nerves that carry the sound signals from the cochlea to the cochlear nucleus. The ABI electrode array contains electrodes that are carried on a pad which is placed on the cochlear nucleus of the auditory brainstem. This positioning enables the electrodes to stimulate acoustic nerves by means of electrical signals.

Conventional ABIs typically include an external speech processor that processes analog signals provided by one or more microphones that receive sound present in the recipient's environment. The speech processor generates coded signals which are transcutaneously provided to an implanted stimulator unit to cause the stimulator to deliver stimulation signals via the implanted electrodes.

SUMMARY

In accordance with one aspect of the invention, a conformal electrode pad for a stimulating medical device is disclosed. The electrode pad comprises a planar base substrate having one or more high-flexibility regions and one or more low-flexibility regions; and one or more electrodes each fixed in position in, and supported by, said one or more less flexible regions. In one embodiment, wherein said medical device comprises an auditory brainstem implant (ABI), and said electrode pad has sufficient flexibility to conform to the cochlear nucleus of a recipient's auditory brainstem such that said one or more electrodes may optimally stimulate the auditory nerves while ensuring said ABI pad maintains structural integrity over its anticipated operational life.

BRIEF DESCRIPTION OF THE DRAWINGS

The invention will be described in conjunction with the accompanying drawings, in which:

FIG. 2A is a simplified schematic front view of an electrode pad in accordance with certain embodiments of the present invention;

FIG. 2B is a simplified schematic front view of an electrode pad in accordance with certain embodiments of the present invention;

FIG. 4 is a front view of a conformal auditory brainstem implant electrode pad in accordance with an embodiment of the present invention;

DETAILED DESCRIPTION

Aspects of the present invention are generally directed to a conformal electrode pad for stimulating medical devices such as an auditory brainstem implant (ABI). Embodiments of the conformal electrode pads of the present invention have a configuration and composition to provide the electrode pad with sufficient flexibility to permit the pad to be curved, molded or otherwise substantially conformed to the cochlea nucleus or other therapeutically-beneficial site, while ensuring the ABI pad maintains structural integrity over its anticipated operational life.

As noted, ABIs are a type of implantable prosthetic hearing device in which the electrode array is surgically implanted in the brain of a hearing impaired person who has deficient or absent auditory nerves that carry signals from the cochlea to the brain. The ABI electrode pad comprises a thin, planar base substrate having one or more high-flexibility regions and one or more low-flexibility regions. The electrodes are fixed in position in, and supported by, the less flexible region(s) while the high-flexibility region(s) provides the ABI electrode pad flexibility, allowing it to conform to the cochlear nucleus of a recipient's auditory brainstem so that the electrodes may optimally stimulate the auditory nerves.

There are several advantages to having an ABI pad that has sufficient flexibility to conform to the cochlear nucleus. For example, the cochlear nucleus is curved and lubricious. As a result, a flat surface contacts only the apex of the curvature. Such minimal contact, in combination with the slippery surface, encourages slippage of the ABI electrode pad from its implanted position. Furthermore, a substantially planar surface may place certain electrodes at a distance from the brainstem surface. Under such circumstances, the electrodes are not precisely positioned adjacent to the desired nerves. As a result, the effectiveness of the stimulation may be significantly reduced. An essential feature of multi-channel prosthetic hearing implants is tonotopic mapping. The intention is that different electrodes produce a stimulus which is perceived as a different frequency. When the electrodes are further from the nerves there is more overlap in their electric fields and hence less chance that adjacent electrodes will stimulate differentiable frequency responses.

This greater distance also requires greater current to be applied to induce a perceived loudness of the stimulus. This increases the likelihood of unintended stimulation of adjacent nerves. In other words, the likelihood of unintentional stimulation of nearby nerves increases as the distance between the electrode and target nerve increases, particularly because greater current must be applied to effect stimulation.

Figure 1A:
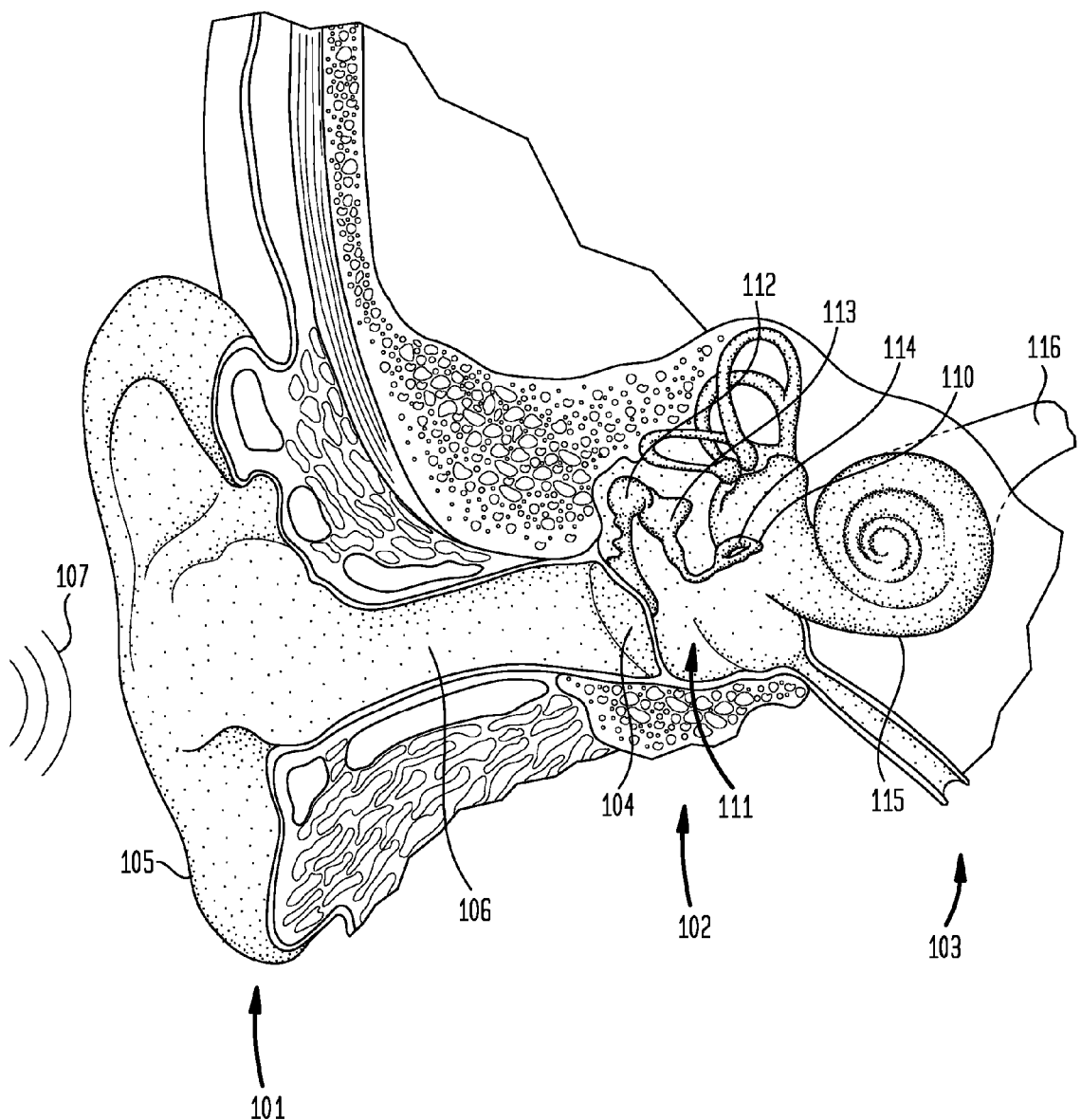
FIG. 1A is a partial section of a human ear showing the important elements in hearing.
Figure 1B:
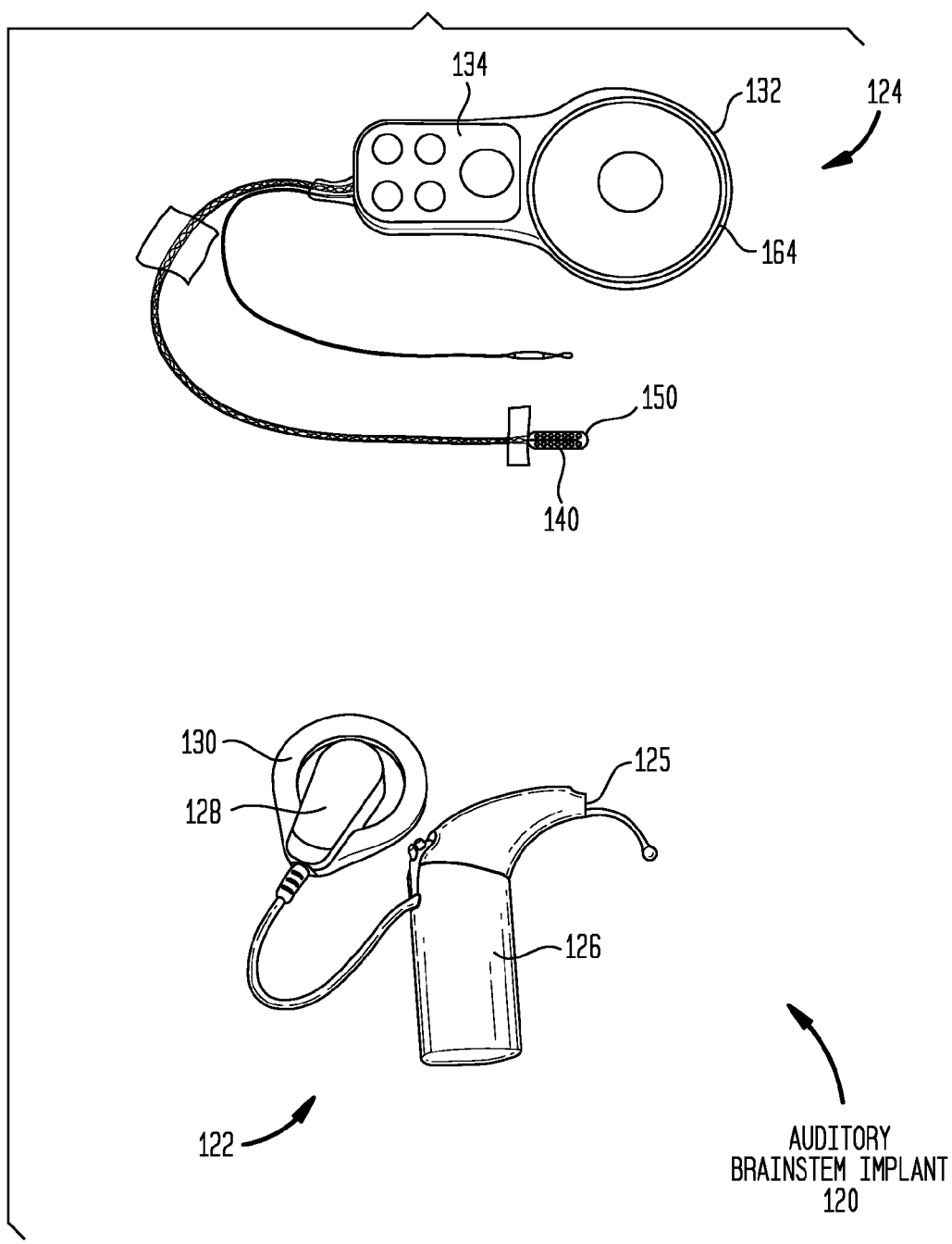
FIG. 1B is a perspective view of the components of the auditory brainstem implant (ABI) in which embodiments of the present invention may be advantageously implemented.

As noted, embodiments of the electrode pad of the present invention may be implemented in many different stimulating medical devices now or later developed. FIG. 1A is a cutaway view of the human ear. FIG. 1B is a perspective views of an illustrative embodiment of an exemplary stimulating medical device in which embodiments of the present invention may be implemented, namely an exemplary auditory brainstem implant (ABI).

In fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates tiny hair cells (not shown) that line the inside of cochlea 115. Activation of the hair cells causes appropriate nerve impulses to be transferred through the spiral ganglion cells and auditory nerve 116 to the brain (not shown), where they are perceived as sound.

In certain persons, there is an absence or destruction of the hair cells. A cochlear implant is utilized in such individuals to directly stimulate the ganglion cells to provide a hearing sensation to such recipients. However, cochlear implants are not suitable for patients with damaged auditory nerves. Such damage may occur, for example, from surgical removal of an acoustic neuroma developed in patients suffering from neurofibromatosis type 2 (NF2). NF2 is a genetic condition characterized by the growth of bilateral acoustic neuromas. As these neuromas enlarge hearing often becomes impaired and the patient may experience additional symptoms, such as tinnitus and facial numbness. When it becomes necessary to surgically remove these benign tumors, portions of the auditory nerves must be removed along with the tumors.

The absence of cochlear nerve 116 rules out the standard cochlear implant. Accordingly, the auditory brainstem implant (ABI) is a modified cochlear implant, similar in nature to a multi-channel cochlear implant, in which the electrode array is configured to be placed directly into the lateral recess of the fourth ventricle in contact with the cochlear nucleus of the brain.

It should be noted that speech perception benefits of brainstem implants differ from those seen with cochlear implants. Following implant, although recipients can detect speech and other environmental sounds, they generally cannot understand speech without lip reading. Thus, the primary benefits of ABI are environmental sound awareness, speech pattern perception, and enhanced lip-reading abilities.

FIG. 1B is a perspective view of an ABI 120. ABI 120 comprises external component assembly 122 which is directly or indirectly attached to the body of the recipient, and an internal component assembly 124 which is temporarily or permanently implanted in the recipient. External assembly 122 comprises microphone 125 for detecting sound which is outputted to a behind-the-ear (BTE) speech processing unit 126 that generates coded signals which are provided to an external transmitter unit 128, along with power from a power source (not shown) such as a battery. External transmitter unit 128 comprises an external coil 130 and, preferably, a magnet (not shown) secured directly or indirectly in external coil 130.

Internal components 124 comprise an internal receiver unit 132 having an internal coil 164 that receives and transmits power and coded signals. A stimulator unit 134 applies the coded signal to the cochlear nucleus (not shown) via an implanted electrode pad 140. Electrode pad 140 has one or more electrodes 150 configured to be positioned so as to be substantially aligned with portions of tonotopically-mapped cochlea nucleus. Signals generated by stimulator unit 134 are typically applied by electrodes 150 to the cochlea nucleus to cause a hearing percept.

As one of ordinary skill in the art will appreciate from the present disclosure, embodiments of the present invention may be advantageously implemented in a variety of devices as described elsewhere herein. Although the ABI described above with reference to FIG. 1B is a partially-implantable device, embodiments of the present invention provide particular benefits to devices which have limited sources of power such as fully-implantable prosthetic hearing devices, as well as other stimulating medical devices now or later developed.

Figure 2C:
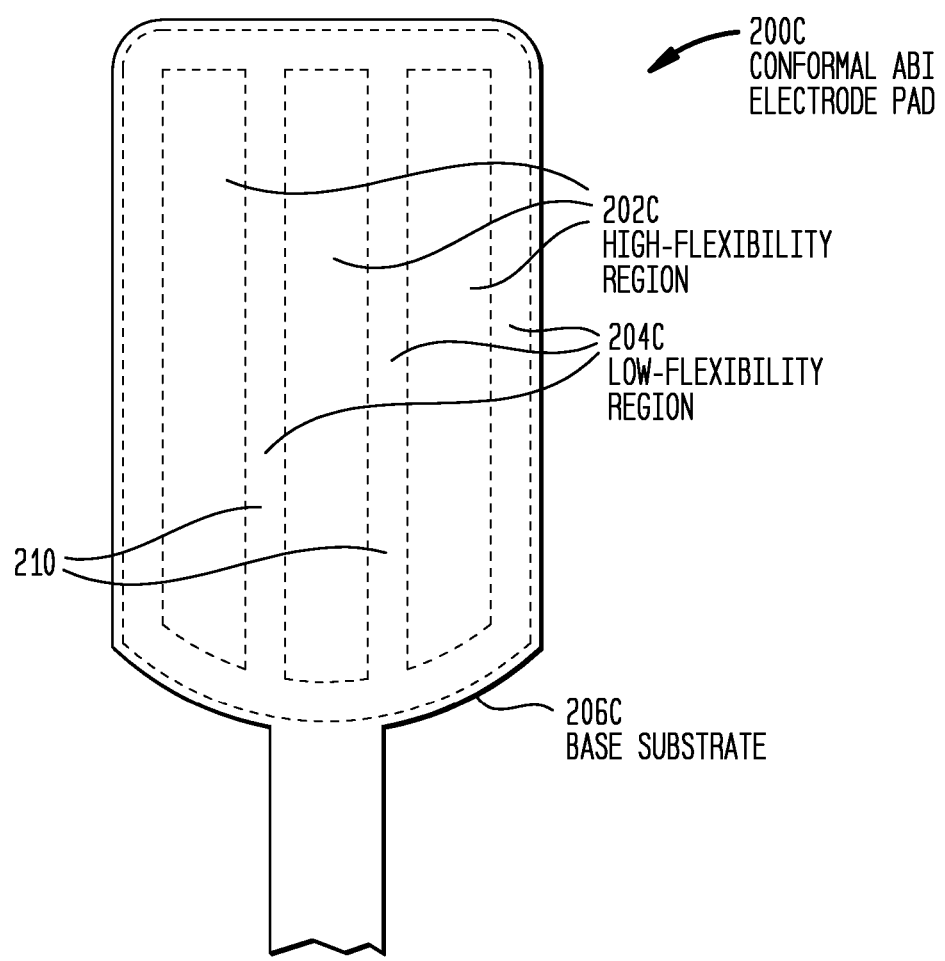
FIG. 2C is a simplified schematic front view of an electrode pad in accordance with certain embodiments of the present invention.

FIGS. 2A through 2C are schematic front views of various embodiments of conformal ABI electrode pads of the present invention. As noted, conformal electrode pads of the present invention comprise a relatively thin base substrate 206 having one or more high-flexibility regions 202 and one or more low-flexibility regions 204. Electrodes (not shown) are fixed in position in, and supported by, low-flexibility region(s) 204. On the other hand, high-flexibility region(s) 202 provides the conformal electrode pads flexibility, allowing the pads to conform to the cochlear nucleus or other site so that the electrodes may optimally stimulate the desired anatomical region.

In FIG. 2A, a single high-flexibility region 202A is located in the approximate center of conformal ABI electrode pad 200A while a single low-flexibility region 204A is located around the perimeter of electrode pad 200A. In FIG. 2B, a portion 208 of low flexibility region 204 extends laterally across electrode pad 200. As such, this embodiment of electrode pad 200B comprises two high-flexibility regions 202B as shown in FIG. 2B. In FIG. 2C, portions 210 of low flexibility region 204 extend longitudinally across electrode pad 200. As such, this embodiment of electrode pad 200C comprises three non-contiguous high-flexibility regions 202C.

It should be appreciated to those of ordinary skill in the art that neither high-flexibility regions 202 nor low-flexibility regions 204 need be contiguous and may take on any configuration and may be located at any location on electrode pad 200 suitable for the particular application.

FIGS. 3A-3D are simplified perspective views of embodiments of electrode pads of the present invention. Note that in all these figures, no details of the electrode pad are illustrated; rather, these simplified figures illustrate the flexibility provided by embodiments of the present invention which enable an implementing electrode pad to conform to a desired stimulation site in a recipient.

Figure 3A:
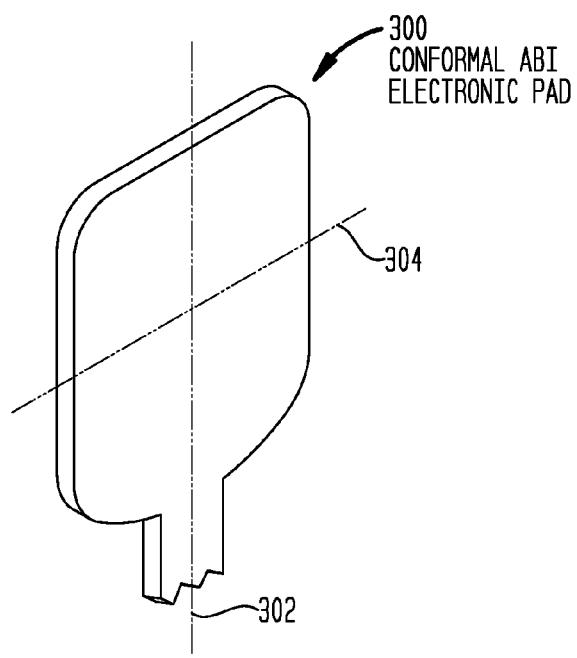
FIG. 3A is a simplified perspective view of an electrode pad of the present invention showing its longitudinal and lateral axes.
Figure 3B:
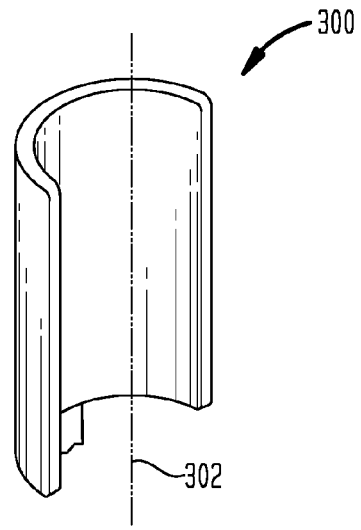
FIG. 3B is a simplified perspective view of an electrode pad of the present invention showing it flexing about its longitudinal axis.
Figure 3C:
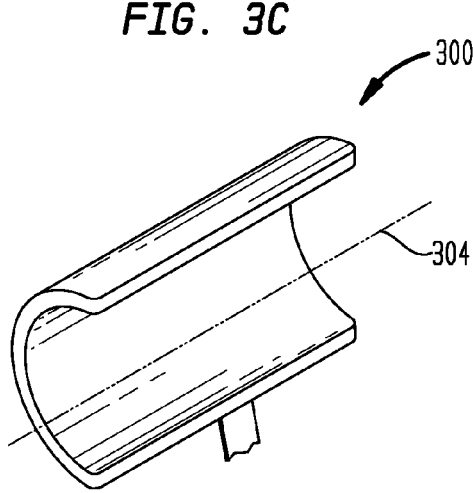
FIG. 3C is a simplified perspective view of an electrode pad of the present invention showing it flexing about its lateral axis.
Figure 3D:
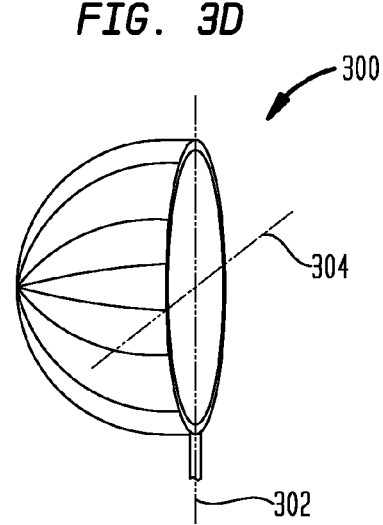
FIG. 3D is a simplified perspective view of an electrode pad of the present invention showing it flexing about its longitudinal and lateral axes.

Referring to FIG. 3A, electrode pad 300 defines longitudinal and lateral axes 302, 304, respectively. In FIG. 3B, electrode pad 300 is shown flexing about its longitudinal axis 302. Similarly, in FIG. 3C electrode pad 300 is shown flexing about its lateral axis 304. In FIG. 3D, electrode pad 300 is shown flexing about its longitudinal axis 302 and its lateral axis 304 to form a cup-shaped pad. In all these embodiments, the depicted flexibility is due to the presence of one or more appropriately-located high-flexibility regions 202 and low-flexibility regions 204 in electrode pad substrate 206.

As noted, electrodes are fixed in position in, and supported by, low-flexibility region(s) 204 while the high-flexibility region(s) provides the ABI electrode pad flexibility, allowing it to conform, for example, to the cochlear nucleus of a recipient's auditory brainstem so that the electrodes may optimally stimulate the auditory nerves.

The difference in flexibility of each of the high-flexibility regions 202 and low-flexibility regions 204 may be due to differences in one or more characteristics of each. For example, in one embodiment such difference in flexibility is attained by differences in thickness or quantity of the same or different material having the same or different durometer, the presence or absence of supporting infrastructure such as rigid inserts and the like, or any combination thereof.

In certain embodiments, for example, ABI pads of the present invention have a durometer of about 30 and a thickness of less than or equal 0.0.7 mm. 0.7 mm. Exemplary embodiments of the ABI pads disclosed herein have an overall dimension generally in the range of about 2.5 by 8 mm. In certain embodiments, a minimal amount of silicone, or other base substrate material, is utilized to protect the electrodes and leads, and the ABI pads may have a width only slightly greater than that required to support the electrodes. The thickness of the ABI pads may be dependent on the base substrate material as well as the requisite flexibility and desired longevity of the electrode pad.

In other embodiments, the durometer is greater than 30. Likewise, in other embodiments, the thickness of the ABI pad is less than or greater than 0.7 mm. The selection of the hardness is determined by a tradeoff between flexibility and durability. The lower the hardness, the shorter the life-span of the pad; for example, a 30 durometer silicone may have a life span of about 70 years. Although harder materials will typically provide longer life spans, their flexibility is reduced correspondingly. This reduction of flexibility may be limited or compensated for by a reduction in the thickness in the ABI pad. As plastics technology advances, enabling harder materials to increase in flexibility, the hardness of the material selected for manufacture may then be increased, as will be evident to those skilled in the art.

Embodiments of an ABI electrode pad of the present invention are described next below with reference to FIGS. 4 through 8. In each of these embodiments, reference to the high- and low-flexibility region(s) will be made using the reference numerals of FIGS. 2A-2C; that is, reference numeral 202 for high-flexibility region(s) and reference numeral 204 for low-flexibility region(s). The elements of the particular electrode pad that form such regions, however, will be referenced with a reference numeral beginning with the figure in which the element is depicted.

FIG. 4 is a front view of one embodiment of an ABI electrode pad of the present invention, referred to herein as ABI electrode pad 400. ABI pad 400 has a base substrate 406 manufactured from silicone or other biocompatible material. Base substrate 406 has a high-flexibility region 202 in the central area of ABI pad 400. In this illustrative embodiment, high-flexibility region 202 is formed with an aperture 410 in the interior region of base substrate 406 and a low-flexibility region 204 which surrounds aperture 410.

Aperture 410 has a pattern comprising a central area 410A and fingers 410B extending laterally outward from central area 410A toward the perimeter of conformal ABI electrode pad 400. The width of central area 410A of aperture 410 and the placement of fingers 410B is not critical and serves to remove base substrate material to increase the flexibility of ABI pad 400. Therefore the wider and longer central area 410B and the greater the number, length and width of fingers 410B, the more flexible pad 400 will be. It should be noted that although eight electrodes 408 are illustrated in this and other figures herein, a lesser or greater number of electrodes may be used, depending upon the application, and the number and placement will be evident to those skilled in the relevant art.

ABI pad 400 has a series of electrodes 408 and connecting leads 412 embedded within base substrate 406 of ABI pad 400. Low-flexibility region 204 has sufficient structural integrity to reliably support electrodes 408 and associated connecting leads 412, and has a durometer sufficient to ensure the durability of ABI pad 400 over its anticipated operational life. Low-flexibility region 204 is molded from, for example, industry standard 30 durometer silicone, and wires 412 and electrodes 408 may be fabricated from industry standard platinum or a platinum/iridium alloy or other bio-compatible noble metals.

To attain the desired flexibility, the thickness or cross section of base substrate 406 is as minimal as possible to increase flexibility while not adversely affecting the noted durability of ABI pad 400. In one embodiment, ABI pad 400 has a thickness of less than or equal 0.7 mm; in another embodiment, less than 0.5 mm.

Figure 5:
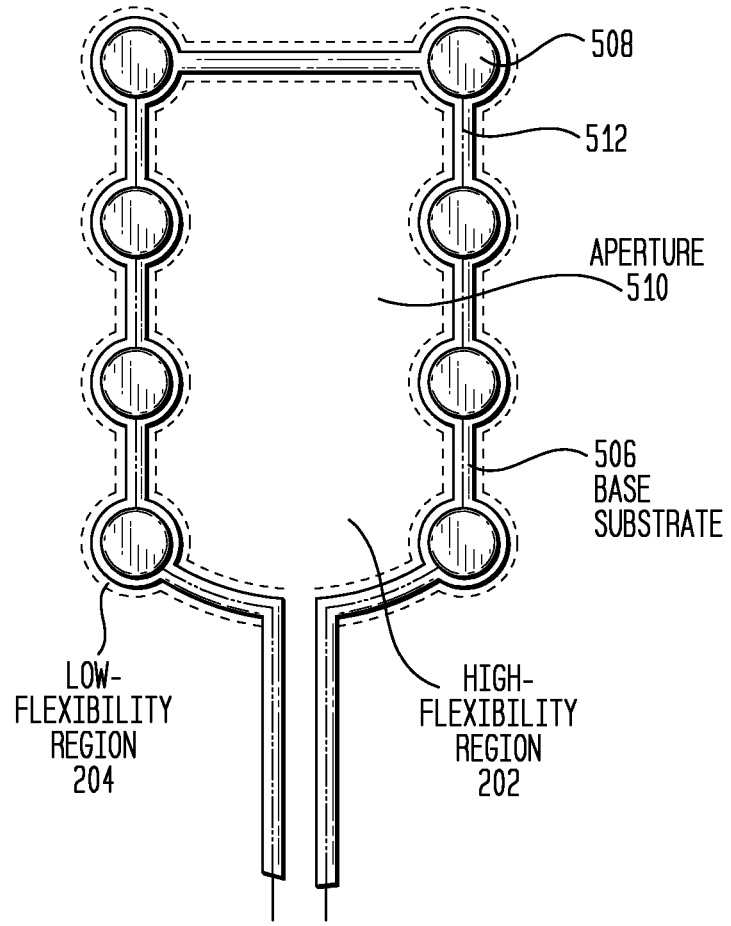
FIG. 5 is a front view of a conformal auditory brainstem implant electrode pad in accordance with an embodiment of the present invention.

FIG. 5 is a front view of one embodiment of an ABI electrode pad of the present invention, referred to herein as ABI electrode pad 500. ABI pad 500 has a high-flexibility region 202 centrally located on ABI pad 500, and a low-flexibility region 204 around the perimeter of ABI pad 500. High-flexibility region 202 is formed by an aperture 510 in base substrate 506. Aperture 510 is dimensioned so that low-flexibility region 204 of ABI pad 500 only has sufficient width, or mass, to embed electrodes 508 and leads 512. In the embodiment illustrated in FIG. 5, the mass of substrate 506 is reduced due to low-flexibility region 202 narrowing when adjacent to leads 512 and increasing when necessary to accommodate electrodes 508. This embodiment provides substantial flexibility and may require use of a tool for implantation, such as the tool disclosed hereinafter, for placement.

Figure 6:
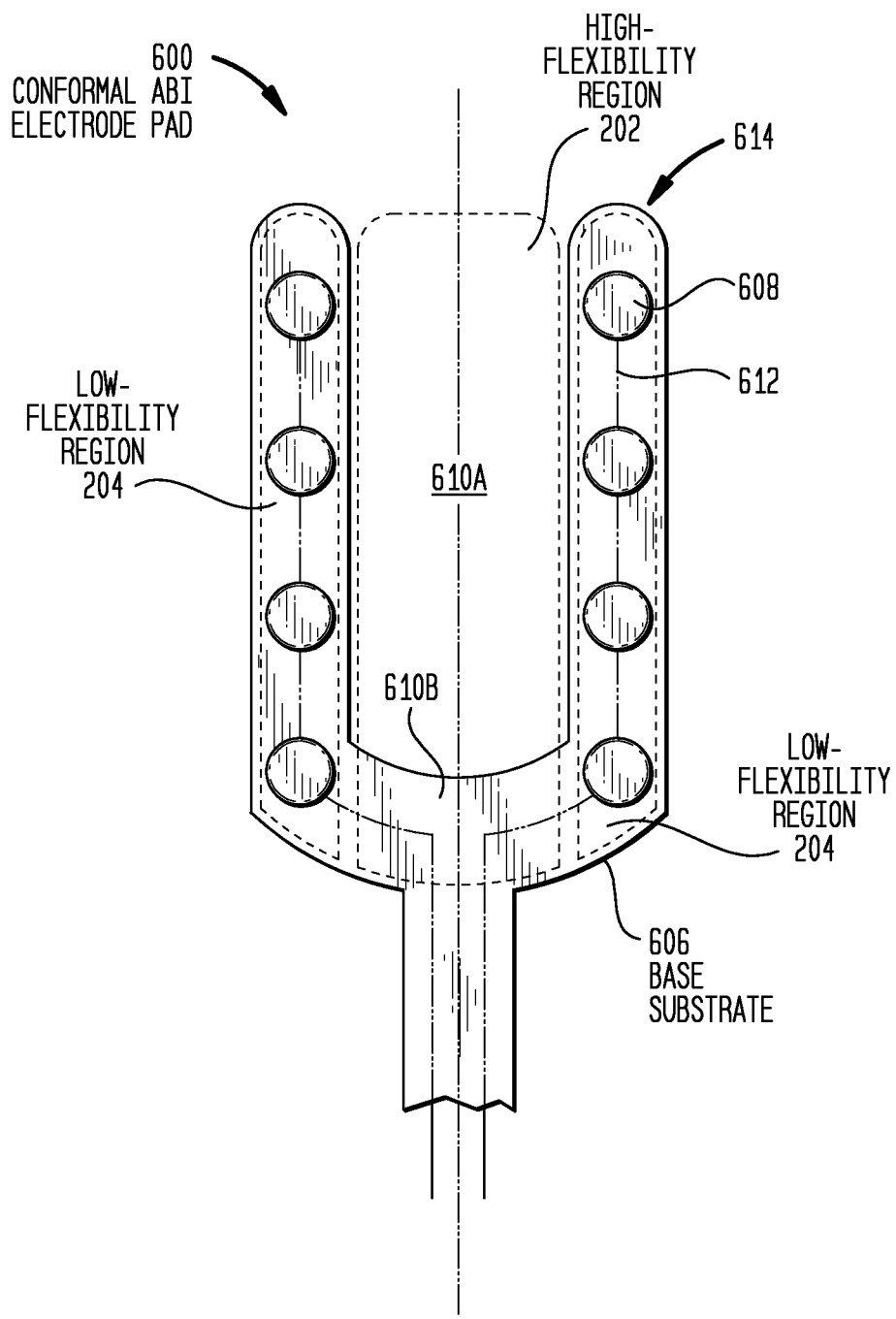
FIG. 6 is a front view of a conformal auditory brainstem implant electrode pad in accordance with an embodiment of the present invention.

FIG. 6 is a front view of one embodiment of an ABI electrode pad of the present invention, referred to herein as ABI electrode pad 600. ABI pad 600 has a base substrate 606 manufactured in the shape similar to that of a tuning fork with an open distal end 614. ABI pad 600 has a high-flexibility region 202 centrally located on ABI pad 600, and low-flexibility regions 204 on opposing sides of base substrate 606. In this embodiment, high-flexibility region 202 is formed by an aperture 610A in base substrate 606 and a portion 610B of base substrate 606. Region 610B of base substrate 606 has greater flexibility than low-flexibility region 204. Such different in flexibility may be attained by implementing different materials, different supporting elements, different thicknesses, etc.

In this illustrative embodiment, low-flexibility regions 204 of ABI pad 600 are substantially uniform in width, with leads 612 and electrodes 608 centered along the length of each low-flexibility region 204. It should be noted, however, that base substrate 606 may also be manufactured to undulate as illustrated in FIG. 5 with distal end 614 remaining open. There are many alternative embodiments of this basic design. These include one or more arms that are shaped in a serpentine pattern, or a wavy pattern and any number of combinations of straight and curved sections.

Figure 7:
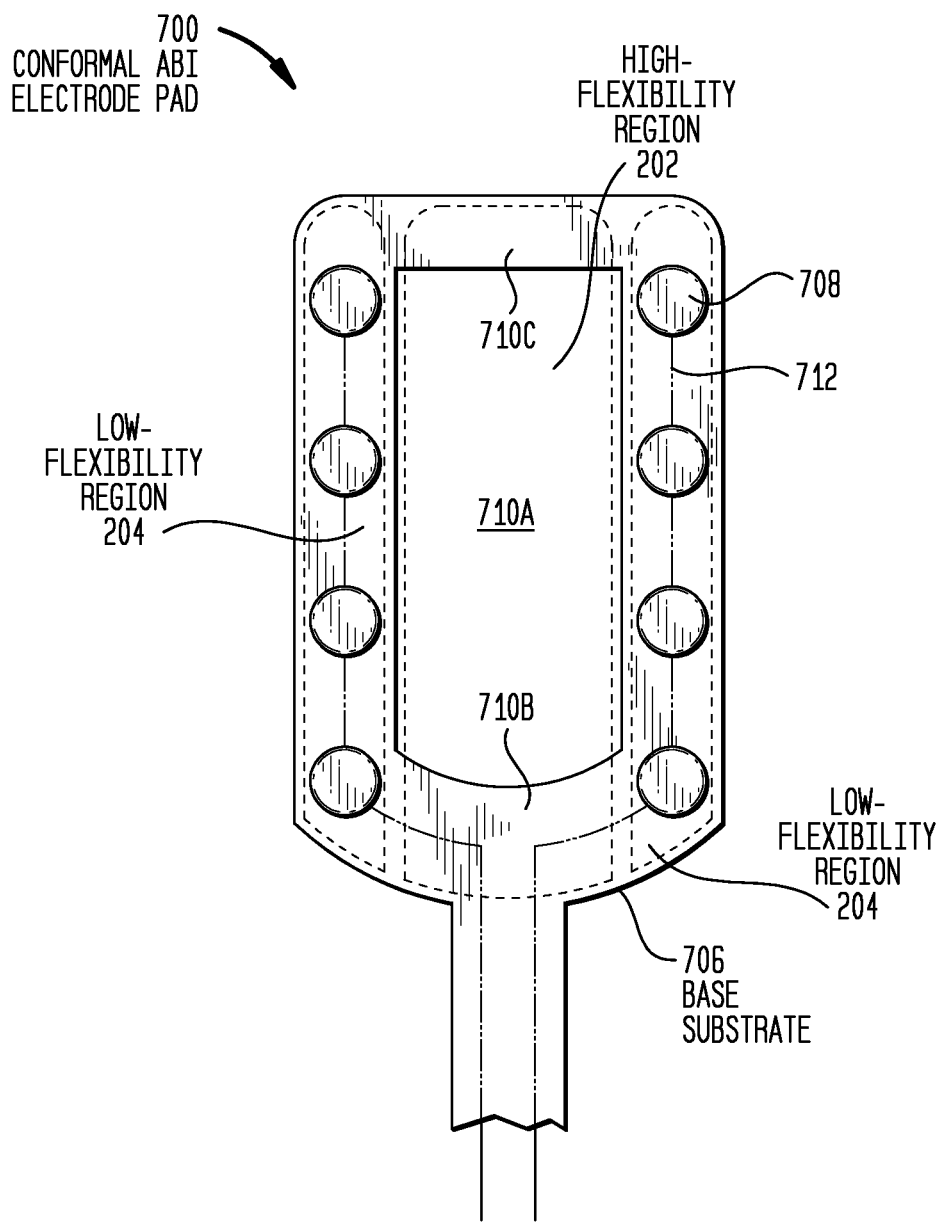
FIG. 7 is a front view of a conformal auditory brainstem implant electrode pad in accordance with an embodiment of the present invention.

FIG. 7 is a front view of one embodiment of an ABI electrode pad of the present invention, referred to herein as ABI electrode pad 700. ABI pad 700 has a high-flexibility region 202 centrally located on ABI pad 700, and low-flexibility regions 204 on opposing sides of high-flexibility region 202. High-flexibility region 202 is formed by an aperture 710A in base substrate 706, as well as high-flexibility portions 710B and 710C of base substrate 706. In this embodiment, low-flexibility regions 204 of base substrate 706 each have substantially parallel interior and exterior perimeters, with electrodes 708 and leads 712 centrally embedded within.

It should be appreciated that the embodiments illustrated herein are exemplary only and other embodiments may be implemented with different high- and low-flexibility regions having different arrangements, dimensions, etc., which provide a desired flexibility in particular directions. Preferably, embodiments of the present invention applicable to ABIs have a combination of high- and low-flexibility regions such that robustness is sufficient for the intended use and operational life. It should also be appreciated that the exact arrangement is dependent on the anticipated end use and surgeon preference as long as reasonable coverage of the receiving surface, such as the brainstem, is obtained. Other examples of layouts can include, but are not limited to, one line, two lines, n lines, lines may be joined top and bottom or only one end, two lines crossing, n lines crossing, circle, or multiple circles (concentric or otherwise).

A variety of wire configurations may also be used to determine the required flexibility, resilience and bending properties. For example, wire cross sections may be round, elliptical, square or other shape and may be a combination of these cross-sectional shapes. Wires may also be laid in a straight, helix, wavy or zig-zag form or any combination of these shapes. It is also possible to use multiple wires for each contact to influence the flexibility. Wires may also be formed from thin-film production techniques as disclosed in a number of previous patents by Cochlear Limited. Wires may also be of various metallic compositions to set the flexibility and resilience. For example, platinum-iridium alloys commonly used in implantable devices make wires that are substantially stronger and only slightly stiffer than pure platinum wires.

Some embodiments of the ABI pads of the present invention are designed to be manufactured using current machinery and production processes, thereby eliminating the need to change equipment. Additionally, because of the reduction in material mass, the ABI pads will use less material and, therefore, reduce material costs.

Figure 8:
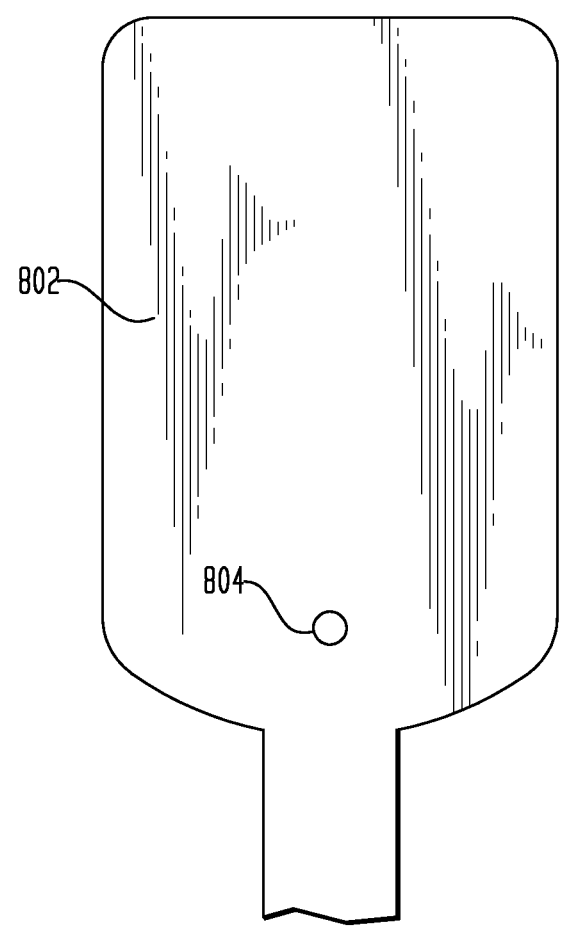
FIG. 8 is a front view of a placement tool to enable rapid and accurate placement of the disclosed auditory brainstem implant pads in accordance with an embodiment of the present invention.
Figure 9:
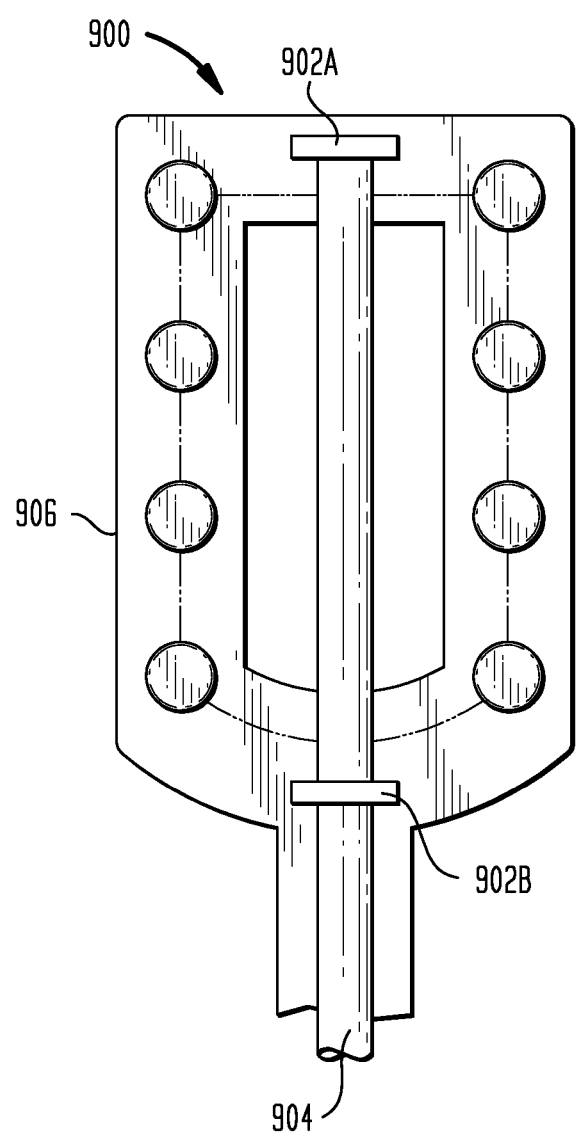
FIG. 9 is a front view of an alternate placing mechanism wherein loops contained within the auditory brainstem implant pad hold the pad to a stylet in accordance with an embodiment of the present invention.

Due to the increased flexibility of the conformal electrode pads of the present invention, a placement tool may be desired or required to facilitate rapid and accurate placement of certain embodiments of the conformal electrode pads. FIG. 8 is a front view of one embodiment of a placement tool 800. Placement tool 800 is a paddle type device that is used to place conformal ABI electrode pads 400, 500, 600, 700 over, and then released onto, the cochlear nucleus of a recipient's brainstem. Such ABI pads may be maintained in place by a releasable pin mechanism where pulling the pin (not shown) from hole 804 in paddle 802 releases the pad onto the brainstem.

Alternatively ABI pads 400, 500, 600, 700 may be affixed to the underside of placement tool 800 by resorbable glue so that when the pad is placed on the brainstem, the body fluids moisten the glue and the ABI pad is released. Paddle 802 of placement tool 800 is preferably curved to proximate the curvature of a brainstem. It will be obvious that the curvature cannot be exactly that of the brainstem, however an approximation enables the ABI pad to be curved upon placement. This is especially important when the method of adhering the ABI pad to paddle 802 is through glue as it exposed more of the ABI pad to the moist surface and facilitates the release. The physical extent of the glue holding the ABI pad to the tool and characteristics of the resorbable glue may be designed to ensure pad releases effectively and within an appropriate time.

In certain embodiments, placement tool 800 has about the same dimensions as the ABI pad being used and can be manufactured from any bio-compatible material. As it is being used to place the ABI pad, a stiffer material than used for the ABI pad would generally be used. A stiff silicone above durometer 30, and preferably durometer 60, may be suitable, however the preferred material would be rigid such as a bio-compatible plastic or metal.

It is critical that the ABI pad be firmly attached to the placement tool 800 and that the ABI pad can, once positioned, be easily and reliably released. In FIG. 8, another method of accomplishing this, through a releasable pin 804, is illustrated that is positioned to "catch" the ABI pad at an open area proximate the area where the wires exit. The release mechanism for the releasable pin 804 may be any of those known in the art which can be incorporated into the placement tool 800 in the appropriate scale.

It should be noted that although the material of manufacture is referred to herein as silicone, any other flexible biocompatible material can be used. It would also be possible to manufacture the pad without the support provided by the silicone and to use a bio-compatible polymer or co-polymer insulation material on the wires and electrodes, as seen in certain of the above embodiments. Examples of bio-compatible insulation materials would be parylene, PTFE, and nylon. In this design, the insulation material, at a thickness of about 10 microns, could alternatively be placed only on the non-brainstem side of the electrodes with the non-insulated electrodes contacting the brainstem. Although this design would be extremely flexible, robustness issues may arise. This may be mitigated by using thicker wires or platinum-iridium wires. Typically wires of 25 or 33 microns would be used in pads 10-40. In one conformal ABI electrode pad a larger wire diameter could be used. This design would also require use of the placement tool similar to that disclosed herein in FIG. 8 as its flexibility would make it difficult to handle.

An alternative method of implanting an ABI electrode pad of the present invention would be through the use of a stylet 904 placed through ABI loops 902A and 902B of a placement tool 900. Stylet 904 is used as the handle with which to place the ABI pad. Once in place stylet 904 is slid from loops 902 and removed, leaving the pad in position. As there would be less support from using stylet 904 than using the placement tool 800, the ABI pad would need to be of a more rigid design. Obviously this concept could be extended to include multiple stylets.

Figure 10:
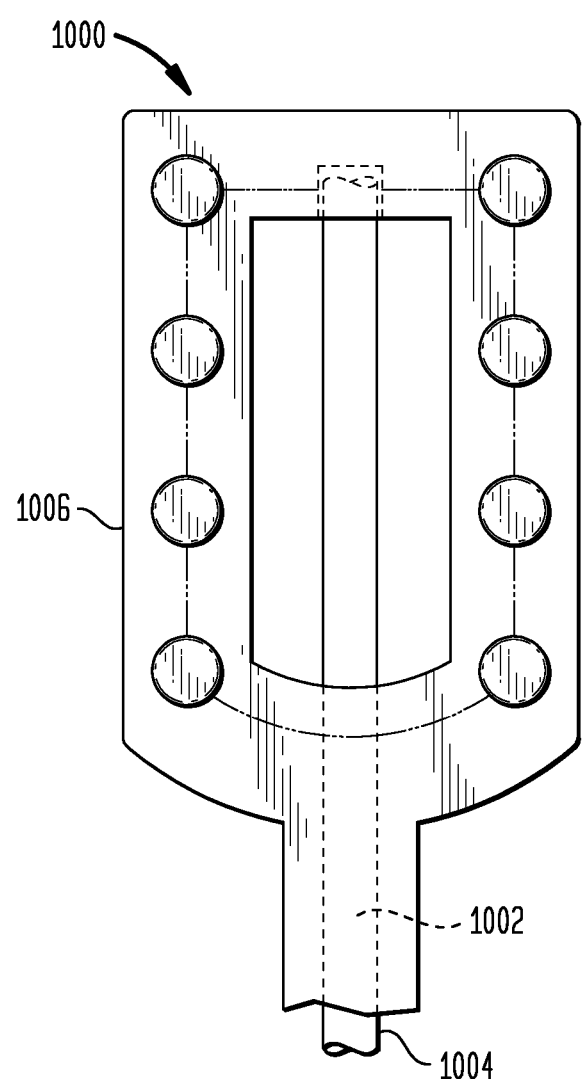
FIG. 10 is a front view of another placement mechanism incorporating a lumen within the auditory brainstem implant pad in accordance with an embodiment of the present invention.

In FIG. 10 a lumen 1002 is molded into an ABI pad 1000 which is dimensioned to carry a carrier 1004, such as a rigid wire or stylet. Once in place, carrier 1004 is removed from lumen 1002. As lumen 1002 is part of pad 1000, the dimensioning and flexibility must be such that it is compatible with the subject ABI electrode pad.

It should be noted that a critical element for all of the forgoing placement tools is visibility to the site of interest. Therefore, an angle, depending upon the end use, may need to be incorporated so that the surgeon's hand is not in the line of sight. The appropriate angles required for the placement of the pad upon the receiving surface will dependent upon end use and will be known to those skilled in the art.

Although discussed herein with respect to the application of ABIs, embodiments of the present invention may be adapted to other areas requiring electrode implants to conform, for example, to a lubricious surface. One such area is retinal implants that will hopefully enable people blinded by retinal degenerative diseases to have at least some of their sign restored. Retinal implants replace the signal-processing functions of a healthy retina to provide input to the retinal nerve cells. These signals then provide input to the optic nerve and the brain. The flexibility of the disclosed pad, providing an ability to adhere to curved, lubricious surfaces, would be advantageous for use in retinal, as well as other, implants.

Further features and advantages of the present invention may be described in U.S. Provisional Patent Application No. 60/738,596 entitled "Flexible Auditory Brainstem Implant Pad," filed on Nov. 22, 2005, and which is hereby incorporated by reference herein.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. An auditory brainstem implant (ABI) pad configured to conform to the cochlear nucleus of a recipient's auditory brainstem, the ABI pad comprising:
   a planar base substrate having at least one low-flexibility region forming at least a portion of the perimeter of the ABI pad, and at least one high-flexibility region forming a central region of the ABI pad; and
   first and second electrodes disposed in, and supported by, said at least one low-flexibility region, wherein said first and second electrodes are disposed on opposite sides of said at least one high-flexibility region.

2. The ABI pad of claim 1, wherein said at least one high-flexibility region has greater flexibility than said at least one low-flexibility region due to differences in any one or more characteristics of the group comprising:
   thickness of base substrate;
   quantity of base substrate material;
   type of base substrate material;
   durometer of respective base substrate materials; and
   supporting infrastructure.

3. The ABI pad of claim 1, wherein said base substrate has a durometer of about 30.

4. The ABI pad of claim 1, wherein said base substrate has a thickness of less than or equal to 0.7 mm.

5. The electrode pad of claim 1, wherein said at least one high-flexibility region comprises an aperture.

6. The electrode pad of claim 5, wherein said aperture comprises:
   a central area; and
   fingers extending from said central area toward a perimeter of said electrode pad.

7. The ABI pad of claim 1, wherein said ABI pad comprises a proximal end, a distal end, and first and second low-flexibility regions that each extend between said proximal end and said distal end of said electrode pad.

8. The ABI pad of claim 1, wherein the planar base substrate is configured to maintain the electrodes in a position adjacent the cochlear nucleus.

9. The ABI pad of claim 1, further comprising:
   a plurality of electrodes, including said first and second electrodes, disposed in, and supported by, said at least one low-flexibility region, wherein said plurality of electrodes includes first and second subsets of said electrodes aligned along first and second portions of the perimeter of the ABI pad, said first and second subsets each include at least two electrodes, and said first and second subsets are disposed on opposite sides of said at least one high-flexibility region.

10. An electrical stimulation device, comprising:
    an auditory brainstem implant (ABI) pad configured to conform to the cochlear nucleus of a recipient's auditory brainstem, the ABI pad comprising:
       a planar base substrate having at least one low-flexibility region forming at least a portion of the perimeter of the ABI pad, and at least one high-flexibility region forming a central region of the ABI pad; and
       first and second electrodes disposed in, and supported by, said at least one low-flexibility region, wherein said first and second electrodes are disposed on opposite sides of said at least one high-flexibility region.

11. The electrical stimulation device of claim 10, wherein said at least one high-flexibility region has greater flexibility than said at least one low-flexibility region due to differences in any one or more characteristics of the group comprising:
   thickness of base substrate;
   quantity of base substrate material;
   type of base substrate material;
   durometer of respective base substrate materials; and
   supporting infrastructure.

12. The electrical stimulation device of claim 10, wherein said base substrate has a durometer of about 30.

13. The electrical stimulation device of claim 10, wherein said at least one high-flexibility region comprises an aperture.

14. The electrical stimulation device of claim 13, wherein said aperture comprises:
   a central area; and
   fingers extending from said central area toward a perimeter of said electrode pad.

15. The electrical stimulation device of claim 10, wherein the planar base substrate is configured to maintain the electrodes in a position adjacent the cochlear nucleus.

16. The device of claim 10, further comprising:
   a plurality of electrodes, including said first and second electrodes, disposed in, and supported by, said at least one low-flexibility region, wherein said plurality of electrodes includes first and second subsets of said electrodes aligned along first and second portions of the perimeter of the ABI pad, said first and second subsets each include at least two electrodes, and said first and second subsets are disposed on opposite sides of said at least one high-flexibility region.

17. An auditory brainstem implant (ABI) pad configured to conform to the cochlear nucleus of a recipient's auditory brainstem, the ABI pad comprising:
   a planar base substrate having first and second low-flexibility regions forming first and second portions of the perimeter of the ABI pad, and at least one high-flexibility region forming a central region of the ABI pad; and
   first and second electrodes disposed in, and supported by, said first and second low-flexibility regions, respectively, wherein said first and second electrodes are disposed on opposite sides of said at least one high-flexibility region,
   wherein the planar base substrate is configured to retain the electrodes in a position adjacent the cochlear nucleus.

18. The ABI pad of claim 17, wherein said at least one high-flexibility region has greater flexibility than said first and second low-flexibility regions due to differences in any one or more characteristics of the group comprising:
   thickness of base substrate;
   quantity of base substrate material;
   type of base substrate material;
   durometer of respective base substrate materials; and
   supporting infrastructure.

19. The ABI pad of claim 17, wherein said base substrate has a thickness of less than or equal to 0.7 mm.

20. The ABI pad of claim 17, further comprising:
   a plurality of electrodes, including said first and second electrodes, each disposed in, and supported by, one of said first and second low-flexibility regions, wherein said plurality of electrodes includes first and second subsets of said electrodes aligned along said first and second portions of the perimeter of the ABI pad, said first and second subsets each include at least two electrodes, and said first and second subsets are disposed on opposite sides of said at least one high-flexibility region.

* * * * *